(12) United States Patent
Gupta et al.

(10) Patent No.: US 8,227,208 B2
(45) Date of Patent: Jul. 24, 2012

(54) PROCESS FOR THE ENANTIOSELECTIVE REDUCTION AND OXIDATION, RESPECTIVELY, OF STEROIDS

(75) Inventors: Antje Gupta, Wiesbaden (DE); Anke Tschentscher, Eltville-Hattenheim (DE); Maria Bobkova, Idstein (DE)

(73) Assignee: IEP GmbH, Wiesbaden (DE)

( * ) Notice: Subject to any disclaimer, the term of this patent is extended or adjusted under 35 U.S.C. 154(b) by 429 days.

(21) Appl. No.: 11/910,886

(22) PCT Filed: Apr. 11, 2007

(86) PCT No.: PCT/EP2007/003197
§ 371 (c)(1),
(2), (4) Date: Jan. 4, 2008

(87) PCT Pub. No.: WO2007/118644
PCT Pub. Date: Oct. 25, 2007

(65) Prior Publication Data
US 2009/0280525 A1   Nov. 12, 2009

(30) Foreign Application Priority Data

Apr. 11, 2006   (AT) .................................. A 627/2006

(51) Int. Cl.
C12P 33/02   (2006.01)
(52) U.S. Cl. ................ 435/61; 435/53; 435/55; 435/89; 435/90
(58) Field of Classification Search ................ 435/53, 435/61, 55, 89, 90
See application file for complete search history.

(56) References Cited

U.S. PATENT DOCUMENTS

| | | | |
|---|---|---|---|
| 5,200,335 A | 4/1993 | Hummel et al. | |
| 5,385,833 A | 1/1995 | Bradshaw et al. | |
| 5,523,223 A | 6/1996 | Kula et al. | |
| 5,523,233 A | 6/1996 | Chartrain et al. | |
| 5,763,236 A | 6/1998 | Kojima et al. | |
| 6,037,158 A | 3/2000 | Hummel et al. | |
| 2004/0214297 A1* | 10/2004 | Davis et al. | 435/128 |
| 2004/0265978 A1 | 12/2004 | Gupta et al. | |
| 2005/0037946 A1* | 2/2005 | Stagliano et al. | 514/1 |
| 2005/0191735 A1* | 9/2005 | Bobkova et al. | 435/135 |
| 2006/0195947 A1* | 8/2006 | Davis et al. | 800/288 |
| 2007/0243594 A1 | 10/2007 | Gupta et al. | |
| 2009/0280525 A1 | 11/2009 | Gupta et al. | |

FOREIGN PATENT DOCUMENTS

| | | |
|---|---|---|
| DE | 10300335 | 7/2004 |
| EP | 1179595 | 2/2002 |
| EP | 1731618 | 12/2006 |
| JP | 03127998 A * | 5/1991 |
| JP | 07231785 | 5/1995 |
| WO | 02/086126 | 10/2002 |
| WO | 03/091423 | 11/2003 |
| WO | 2004/111083 | 12/2004 |

OTHER PUBLICATIONS

Derwent abstract for JP 3127998 (May 31, 1991) downloaded Jan. 3, 2011.*
Flynn et al. J. Pharm. Sci. (1979) 68(9): 1090-1097.*
Pietro Cremonesi et al., Enzymatic Dehydrogenation of Testosterone Coupled to Pyruvate Reduction in a Two-Phase System, J. Biochem., 1974, 401-405, 44.
Pietro Cremonesi et al., Enzymatic Preparation of 20B-Hydroxysteroids in a Two-Phase System, Biotechnology and Bioengineering, 1975, pp. 1101-1108, vol. XVII, John Wiley & Sons, Inc.
Giacomo Carrera et al., Enzymatic reduction of dehydrocholic acid to 12-ketochenodeoxycholic acid with NADH regeneration, Enzyme Microb. Technol., Jul. 1984, 307-310, vol. 6, Butterworth & Co. Ltd.
G. Carrera et al., Enzymatic Preparation of 12-Ketochenodeoxycholic Acid with NADP Regeneration, Biotechnology and Bioengineering, 1984, pp. 560-563, vol. XXVI, John Wiley & Sons, Inc.
Roberto Bovara et al., Enzymatic a/B Inversion of the C-7-Hydroxyl of Steroids, J. Org. Chem., 1993, 499-501, 58, American Chemical Society.
Sergio Riva, et al., Enzymatic a/B Inversion of C-3 Hydroxyl of Bile Acids and Study of the Effects of Organic Solvents on Reaction Rates, J. Org. Chem, 1988, 88-92, 53, American Chemical Society.
Paola Pedrini et al., *Xanthomonas maltophilia* CBS 897.97 as a source of new 7B-and 7a-hydroxysteroid dehydrogenases and cholylglycine hydrolase: Improved biotransformations of bile acids, Steroids, 2006, 189-198, 71.
Guangming Xiong et al., Regulation of the Steroid-inducible 3a-Hydroxysteroid Dehydrogenase/Carbonyl Reductase Gene in *Comamonas testosteroni*, The Journal of Biological Chemistry, 2001, 9961-9970, vol. 276, No. 13, Issue of Mar. 30, The American Society for Biochemistry and Molecular Bioloby, Inc.

(Continued)

*Primary Examiner* — Susan Hanley
(74) *Attorney, Agent, or Firm* — Workman Nydegger

(57) ABSTRACT

A process for the enantioselective reduction of compounds having a steroid structure (ABCD) including one or several heteroatoms, one or several double bonds and/or aromatic components in the ring structure and having at least one oxo group at positions 3, 7, 11, 12 or 17 in the steroid ring system or in the a-position of any carbon moiety of the steroid structure:

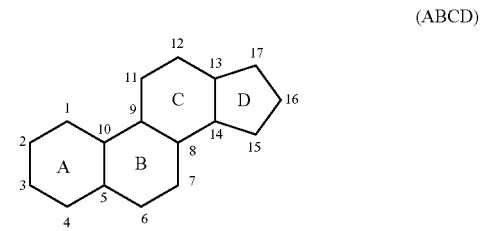

(ABCD)

comprising providing the oxosteroid compound in the reaction at a concentration of ≧50 g/L, a reduced cofactor NADH or NADPH, a hydroxysteroid dehydrogenase and a secondary alcohol or cycloalknaol to effect the enantioselective reduction.

21 Claims, No Drawings

OTHER PUBLICATIONS

Rudolf Edenharder et al., Partial Purification and Characterization of an NAD-Dependent 3B-Hydroxysteroid Dehydrogenase from *Clostridium innocuum*, Applied and Environmental Microbiology, Jun. 1989, 1656-1659, vol. 55, No. 6, American Society for Microbiology.

Manfred Braun et al., 12a-Hydroxysteroid dehydrogenase from *Clostridium* group P, strain C 48-50, Production, purification and characterization, Eur. J. Biochem., 1991, 439-450, 196, EEBS.

Rudolf Edenharder et al., Characterization of NADP-dependent 12B-hydroxysteroid dehydrogenase from *Clostridium paraputrificum*, Biochimica et Biophysica Acta, 1988, 362-370, 962, Elsevier Science Publishers B.V.

Edward S. Szymanski et al., 20B-Hydroxysteroid Oxidoreductase, Kinetics and Binding of Corticosteroids and Corticosteroid-21-Aldehydes, The Journal of Biological Chemistry, 1977, 205-211, vol. 252, No. 1, Issue of Jan. 10.

Amy E. Krafft et al., Purification and Characterization of a Novel Form of 20a-Hydroxysteroid Dehydrogenase from *Clostridium scindens*, Journal of Bacteriology, Jun. 1989, 2925-2932, American Society for Microbiology.

Ayako Inazu et al., Purification and characterization of a novel dimeric 20a-hydroxysteroid dehydrogenase from *Tetrahymena pyriformis*, Biochem. J., 1994, 195-200, 297.

James P. Coleman, Characterization and Regulation of the NADP-Linked 7a-Hydroxysteroid Dehydrogenase Gene from *Clostridium sordellii*, Journal of Bacteriology, Aug. 1994, 4865-4874, vol. 176, No. 16, American Society for Microbiology.a.

Tadashi Yoshimoto, Cloning and Sequencing of the 7a-Hydroxysteroid Dehydrogenase Gene from *Escherichia coli* HB101 and Characterization of the Expressed Enzyme, Journal of Bacteriology, Apr. 1991, 2173-2179, vol. 173, No. 7, American Society for Microbiology.

Michael J. Bennett, Cloning and Characterization of the NAD-Dependent 7a-Hydroxysteroid Dehydrogenase from *Bacteroides fragilis*, Current Microbiology, 2003, 475-484, vol. 47, Springer-Verlag, New York Inc.

Taiko Akao, Purification and Characterization of 7B-Hydroxysteroid Dehydrogenase from *Ruminococcus* sp. of Human Intestine, J. Biochem, 1987, 613-619, 102, No. 3.

Rudolf Edenharder et al., Characterization of NAD-dependent 3a- and 3B-hydroxysteroid dehydrogenase and of NADP-dependent 7B-hydroxysteroid dehydrogenase from *Peptostreptococcus productus*, Biochimica et Biophysica Acta, 1989, 230-238, 1004, Elsevier Science Publishers B.V.

Seiju Hirano et al., Characterization of NADP-Dependent 7B-Hydroxysteroid Dehydrogenases from *Peptostreptococcus productus* and *Eubacterium aerofaciens*, Applied and Environmental Microbiology, May 1982, 1057-1063, vol. 43, No. 5.

Eiji Itagaki et al., Purification and Characterization of 17B-Hydroxysteroid Dehydrogenase from *Cylindrocarpon radicicola*, J. Biochem, 1988, 1039-1044, vol. 103, No. 6.

Tea Lanisnik Rizner, Purification and Characterization of 17B-Hydroxysteroid Dehydrogenase from the Filamentous Fungus *Cochliobolus lunatus*, J. Steroid Biochem. Molec. Biol., 1996, 205-214, vol. 59, No. 2.

Richard M. Schultz, 3(17)B-Hydroxysteroid Dehydrogenase of *Pseudomonas testosteroni*, A Convenient Purification and Demonstration of Multiple Molecular Forms, The Journal of Biological Chemistry, 1977, 3775-3783, vol. 252, No. 11, Issue of Jun. 10.

Donna W. Payne et al., Isolation of Novel Microbial 3a-, 3B-, and 17B-Hydroxysteroid Dehydrogenases, The Journal of Biological Chemistry, 1985, 13648-13655, vol. 260, No. 25, Issue of Nov. 5, The American Society of Biological Chemists, Inc.

Paloma De Prada et al., Purification and characterization of a novel 17a-hydroxysteroid dehydrogenase from an intestinal *Eubacterium* sp. VPI 12708, Journal of Lipid Research, 1994, 922-929, vol. 35.

Jorg Peters et al., A novel NADH-dependent carbonyl reductase with an extremely broad substrate range from *Candida parapsilosis*: Purification and characterization, Enzyme Microb. Technol., Nov. 1993, 950-958, vol. 15, Butterworth-Heinemann.

Sheng-Xue Xie, NAD+-Dependent (S)-Specific Secondary Alcohol Dehydrogenase Involved in Stereoinversion of 3-Pentyn-2-ol Catalyzed by *Nocardia fusca* AKU 2123, Biosci. Biotechnol. Biochem., 1999, 1721-1729, 63, 10.

K. Abokitse et al., Cloning, sequence analysis, and heterologous expression of the gene encoding a (S)-specific alcohol dehydrogenase from *Rhodococcus erythropolis* DSM 43297, Appl Microbiol Biotechnol, 2003, 380-386, 62.

Wolfgang Stampfer, Biocatalytic Asymmetric Hydrogen Transfer Employing *Rhodococcus ruber* DSM 44541, JOC Article, J. Org. Chem, 2003, 402-406, 68, American Chemical Society.

J.H. Abalain, Cloning, DNA Sequencing and Expression of (3-17)B Hydroxysteroid Dehydrogenase from *Pseudomonas testosteroni*, J. Steroid Biochem. Molec. Biol., 1993, 133-139, vol. 44, No. 2.

Riva, S. et al: "Enzymatic alpha/beta Inversion of C-3 Hydroxyl of Bile Acids and Study of the Effects of Organic Solvents on Reaction Rates," Journal of Organic Chemistry, (1988), vol. 53, No. 1, pp. 88-92.

Carrea, G. et al: "Enzymatic oxidoreduction of steroids in two-phase systems: effects of organic solvents on enzyme kinetics and evaluation of the performance of different reactors," Enzyme and Microbial Technology, (1988), vol. 10, No. 6, pp. 333-340.

Cremonesi, P. et al: "Enzymatic Dehydrogenation of Steroids by beta-Hydroxysteroid Dehydrogenase in a Two-Phase System," Archives of Biochemistry and Biophysics, vol. 159, (1973), pp. 7-10.

Riva et al. Preparative-Scale Regio- and Stereospecfic Oxidoreduction of Cholic Acid and Dehydrocholic Acid, J. Org. Chem., 1986, pp. 2902-2906, vol. 51, No. 15.

Karsten Niefind et al., Crystallization and preliminary characterization of crystals of R-alcohol dehydrogenase from *Lactobacillus brevis*, Biological Crystallography, Acta Cryst., 2000, 1696-1698, D56.

Fung, E. et al: "*Cryptococcus neoformans* serotype D sequencying." Database EMBL24, May 2005 (May 24, 2005), XP002407089.

Dayhoff, M. et al.: "A Model of Evolutionary Change in Proteins," Atlas of Protein Sequence and Structure (1978) 5 (3):345-352.

Karlin, S. et al.: Methods for assessing the statistical significance of molecular sequence features by using general scoring schemes, Proc. Natl. Acad. Sci. USA, Mar. 1990, vol. 87, pp. 2264-2268.

Lowry, O. et al.: "Protein Measurement with the Folin Phenol Reagent," J Biol Chem. Nov. 1951; 193(1):265-75.

Peterson, G.: "Review of the Folin Phenol Protein Quantitation Method of Lowery, Rosebrough, Farr, and Randall," Analytical Biochemistry (1979) 100:201-220.

Tishkov, V. et al.: "Pilot Scale Production and Isolation of Recominant NAD+- and NADP+-Specific Formate Dehydrogenases," Biotechnology and Bioengineering, Jul. 20, 1999, vol. 64, No. 2, pp. 187-193.

U.S. Appl. No. 11/996,968, Dec. 22, 2010, Office Action.
U.S. Appl. No. 11/996,968, Jun. 10, 2011, Office Action.
U.S. Appl. No. 11/996,968, Oct. 14, 2011, Notice of Allowance.

* cited by examiner

PROCESS FOR THE ENANTIOSELECTIVE REDUCTION AND OXIDATION, RESPECTIVELY, OF STEROIDS

The present invention relates to a process for the enantioselective enzymatic reduction of compounds which comprise a steroid structure (ABCD) including one or several heteroatoms, one or several double bonds and/or one aromatic component in the ring structure and have at least one oxo group at position 3, 7, 11, 12 or 17 in the steroid ring system or in the α-position at any carbon moiety on the steroid skeleton (=oxosteroid compound), wherein the oxosteroid compound is reduced with a hydroxysteroid dehydrogenase in the presence of a cofactor NADH or NADPH.

Furthermore, the present invention relates to a process for the oxidation of compounds which comprise a steroid structure (ABCD) including one or several heteroatoms, one or several double bonds and/or one aromatic component in the ring structure and have at least one hydroxy group at position 3, 7, 11, 12 or 17 in the steroid ring system or in the α-position at any carbon moiety on the steroid skeleton (=hydroxysteroid compound), wherein the hydroxysteroid compound is oxidized with a hydroxysteroid dehydrogenase in the presence of a cofactor NAD or NADP.

Steroids are compounds which possess the ring system of cholesterol and differ in terms of the number of double bonds, the type, number and position of functional groups, the number of methyl groups, the alkyl side chain and the configuration of bonds. Steroid compounds are found both in the animal organism and in fungi and plants and exhibit manifold biological activities, for example, as male and female sex hormones, as hormones of the adrenal gland, as vitamins, as bile acids, as steroid sapogenines, as cardioactive substances and as toad venoms.

By oxosteroid compounds, steroids of the initially defined kind, i.e., those which have at least one keto function, are hereinafter understood, wherein said function can be included in the ring system or also in a side chain located at the steroid skeleton.

By hydroxysteroid compounds, steroids of the initially defined kind, i.e., those which have at least one hydroxy function, are hereinafter understood, wherein said function can be included in the ring system or also in a side chain located at the steroid skeleton.

Because of the manifold physiological effects of steroids it is obvious that steroid compounds and derivatives are also used, in large numbers, in medicine as therapeutically effective substances and medicaments.

For example, progestogen and estrogen derivatives are used worldwide as contraceptives; androgens (testosterone) are used as anabolics and antiandrogen is used, e.g., in the therapy of prostate carcinomas. Glucocorticoids (cortisone, cortisol, prednisolone and prednisone) and derivatives thereof are widely used in the therapeutic treatment of skin diseases, rheumatic diseases, allergic reactions, renal diseases, gastrointestinal diseases and many other disorders due to their antiphlogistic, antiallergic and immunosuppressive effects.

The global market of biologically active steroid compounds is enormous. In the production of various steroid derivatives having different effects, biotransformations play an important role. In particular, reactions catalyzed by hydroxylases and dehydrogenases are thereby of importance. In this connection, delta-1-dehydrogenation, 11 beta-reduction, 20 beta-reduction, 17 beta-reduction, stereoselective reductions at positions 3 and 7 and also oxidations of hydroxy groups, particularly at positions 3, 7, 12 and 17, play specific roles.

Industrially, bioreductions on steroids have so far been implemented exclusively with whole intact cells and at substrate concentrations of far below 10 g/l. First of all, this is due to the fact that the enzymes responsible for biotransformations have so far not been characterized and been expressible, respectively, and, secondly, that no satisfactory technological solution has been available which remedies, on the one hand, the problem of poor solubility of steroids in an aqueous medium and, on the other hand, the problem of regenerating the cofactors NADH and NADPH to a sufficient degree.

Oxidations on steroids have so far been performed chemically in an industrial manner.

Attempts at an enantioselective reduction of steroids with isolated enzymes were substantially described by G. Carrea from 1975 until 1988 (Eur. J. Biochemistry 44, 1974 p. 401-405; Biotechnology and Bioengineering, Vol 17, 1975, p. 1101-1108; Enzyme Microb. Technol. Vol 6, July, 1984, p. 307-311; Biotechnology and Bioengineering, Vol 26, 1984, p. 560-563; J. Org. Chem 51, 1986, p. 2902-2906; J. Org. Chem. 58, 1993, p. 499-501; J. Org. Chem., 53, 1988, p. 88-92; Enzyme Microb. Technol., Vol 10, June, p. 333-339; Archives of Biochemistry and Biophysics, 159, 1973, p. 7-10).

In doing so, various hydroxysteroid dehydrogenases (HSHD) were used, whereby the regeneration of the cofactor NADH was achieved essentially by coupling with the enzymes lactate dehydrogenase, formate dehydrogenase or also alcohol dehydrogenase from yeast. The regeneration of NADP was effected by means of glucose dehydrogenase. In order to overcome the solubility problems, experiments were also carried out in a two-phase system with ethyl acetate and butyl acetate as the organic phase. Also with isolated enzymes in the two-phase system, the operation was performed in ranges of concentration of usually far below 10 g/l, whereby the "total turn over numbers" (TTN=mol of reduced oxosteroid compound/mol of cofactor used) that were achieved were likewise far below 1000, which is why said processes failed to provide a substantial economic advantage in comparison to whole-cell processes.

In addition, there are papers wherein the conversion of hydroxy groups from 7 alpha to 7 beta was accomplished by coupling oxidation and reduction. This was achieved by coupling 7α HSDH and 7β HSDH (Pedrini et al., Steroids 71 (2006), p. 189-198). Also in this process, the operation was performed in ranges of concentration of far below 10 g/l and the "total turn over numbers" (TTN=mol of reduced oxosteroid compound/mol of cofactor used) achieved were below 100, which is why also these processes are economically not relevant.

The invention aims at avoiding said disadvantages and difficulties and has as its object to provide a process which enables the enantioselective reduction and oxidation, respectively, of oxosteroid compounds and hydroxysteroid compounds, respectively, with higher turnovers, in higher ranges of concentration and with higher TTN of the cofactors and hence in a more economical manner.

With a process of the initially mentioned kind, said object is achieved in that
a) the oxosteroid compound is provided in the reaction at a concentration of $\geq 50$ g/l,
b) the oxidized cofactor NAD or NADP formed by the hydroxysteroid dehydrogenase is regenerated continuously by oxidation of a secondary alcohol of general formula $R_X R_Y CHOH$, wherein $R_X$, $R_Y$ independently represent hydrogen, a branched or unbranched C1-C8-alkyl and $C_{total} \geq 3$, or by oxidation of a C4-C6-cycloalkanol, and c) an additional oxidoreductase/alcohol dehydrogenase is used for the oxidation of the secondary alcohol of general formula $R_X R_Y CHOH$ or of the cycloalkanol, respectively.

In a further process of the initially mentioned kind, said object is achieved in that a) the hydroxysteroid compound is provided in the reaction at a concentration of $\geq 50$ g/l, b) the reduced cofactor NADH or NADPH formed by the hydroxysteroid dehydrogenase is regenerated continuously by reduction of a keto compound of general formula $R_X R_Y CO$, wherein $R_X$, $R_Y$ independently represent hydrogen, a branched or unbranched C1-C8-alkyl and $C_{total} \geq 3$, or by reduction of a C4-C6-cycloalkanone, and c) an additional oxidoreductase/alcohol dehydrogenase is used for the reduction of the keto compound of general formula $R_X R_Y CO$ or of the cycloalkanone, respectively.

The present invention constitutes a substantial improvement of the enantioselective enzymatic reduction and oxidation reactions at the steroid skeleton as compared to the prior art. The present invention enables the reduction and oxidation, respectively, of oxosteroid compounds to the corresponding hydroxysteroids with free enzymes in ranges of concentration which by far exceed those described in the prior art.

In the process according to the invention, NADH or NADPH is used as the cofactor. Under the term "NADP", nicotinamide adenine dinucleotide phosphate is understood, by "NADPH", reduced nicotinamide adenine dinucleotide phosphate is understood. The term "NAD" denotes nicotinamide adenine dinucleotide, the term "NADH" denotes reduced nicotinamide adenine dinucleotide.

According to a preferred embodiment, the process according to the invention is characterized in that a compound of general formula I

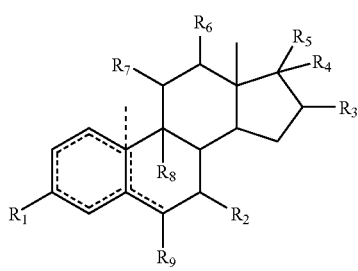

(I)

is used as the oxosteroid compound,
wherein
$R_1$ represents hydrogen, a methyl group, a hydroxy group or an oxo group,
$R_2$ represents hydrogen, a methyl group, a hydroxy group or an oxo group,
$R_3$ represents hydrogen, a hydroxy group, an oxo group or a methyl group,
$R_4$ represents hydrogen or a hydroxy group,
$R_5$ represents hydrogen, a moiety —$COR_{10}$, wherein $R_{10}$ is a C1-C4-alkyl group that is unsubstituted or substituted with a hydroxy group or a substituted or unsubstituted C1-C4-carboxyalkyl group,
or $R_4$ and $R_5$ together represent an oxo group,
$R_6$ represents hydrogen, a methyl group, a hydroxy group or an oxo group,
$R_7$ represents hydrogen, a methyl group, a hydroxy group or an oxo group,
$R_8$ represents hydrogen, a methyl group or a halide, and
$R_9$ represents hydrogen, a methyl group, a hydroxy group, an oxo group or a halide,
wherein at least one of $R_1$, $R_2$, $R_4+R_5$, $R_6$, $R_8$ or $R_9$ is an oxo group, or $R_5$ is a moiety —$COR_{10}$, respectively, and the structural element

represents a benzene ring or a C6-ring having 0, 1 or 2 C—C-double bonds.

According to a preferred embodiment, the process according to the invention is characterized in that a compound of general formula I

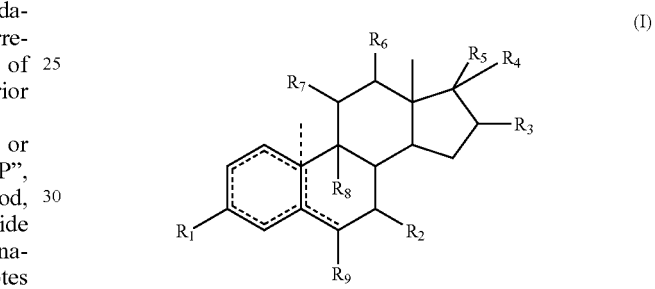

(I)

is used as the hydroxysteroid compound,
wherein
$R_1$ represents hydrogen, a methyl group, a hydroxy group or an oxo group,
$R_2$ represents hydrogen, a methyl group, an oxo group or a hydroxy group,
$R_3$ represents hydrogen, a hydroxy group, an oxo group or a methyl group,
$R_4$ represents hydrogen or a hydroxy group,
$R_5$ represents hydrogen, a moiety —$COR_{10}$, wherein $R_{10}$ is a C1-C4-alkyl group that is unsubstituted or substituted with a hydroxy group or a substituted or unsubstituted C1-C4-carboxyalkyl group,
or $R_4$ and $R_5$ together represent an oxo group,
$R_6$ represents hydrogen, a methyl group, an oxo group or a hydroxy group,
$R_7$ represents hydrogen, a methyl group, an oxo group or a hydroxy group,
$R_8$ represents hydrogen, a methyl group or a halide, and
$R_9$ represents hydrogen, a methyl group, a hydroxy group, an oxo group or a halide,
wherein at least one of $R_1$, $R_2$, $R_4$, $R_6$, $R_7$, $R_8$ or $R_9$ is a hydroxy group and the structural element

represents a benzene ring or a C6-ring having 0, 1 or 2 C—C-double bonds.

2-Propanol, 2-butanol, 2-pentanol, 4-methyl-2-pentanol, 2-hexanol, 2-heptanol, 5-methyl-2-hexanol or 2-octanol is preferably used as the secondary alcohol of general formula $R_xR_yCHOH$, and cyclohexanol is used as the cycloalcohol.

Acetone, 2-butanone, 2-pentanone, 4-methyl-2-pentanone, 2-hexanone, 2-heptanone, 5-methyl-2-hexanone or 2-octanone is preferably used as the ketone of general formula $R_xR_yCO$, and cyclohexanone is used as the cycloalkanone.

In the following, the ketone of general formula $R_xR_yCO$ or the C4-C6-cycloalkanone, respectively, and the secondary alcohol of general formula $R_xR_yCHOH$ or the C4-C6-cycloalkanol, respectively, are summarized under the general term cosubstrate.

The processes according to the invention are preferably carried out in an aqueous organic two-phase system. Thereby, the cosubstrate used for coenzyme regeneration is suitably not miscible with water and thus forms the organic phase of the aqueous organic two-phase system.

According to a further possible embodiment, an organic solvent not involved in the regeneration of the cofactor such as, for example, diethyl ether, tertiary butyl methyl ether, diisopropyl ether, dibutyl ether, ethyl acetate, butyl acetate, heptane, hexane or cyclohexane is additionally employed in the process.

Furthermore, it is preferred that the TTN of the process according to the invention is $\geq 10^3$.

In addition, preferably at least 50% of the employed oxosteroid compound or hydroxysteroid compound, respectively, is reduced to the corresponding hydroxysteroid compound or oxidized to the oxosteroid compound, respectively, within 2 to 96 h.

Preferred embodiments of the process according to the invention are characterized in that, for example, ketolithocholic acid (formula II), dexamethasone (formula III), 4-androstene-3,17-dione (formula IV), 1,4-androstadiene-3,17-dione (formula V), estrone (formula VI), pregnenolone (formula VII) and cortisone (formula VIII) are used as oxosteroid compounds.

Preferred embodiments of the process according to the invention are furthermore characterized in that, for example, various derivatives of bile acid such as cholic acid, chenodeoxycholic acid, 12-oxocholic acid, 3-hydroxy-12-oxocholic acid, ketolithocholic acid, lithocholic acid or also hydrocortisone are used as hydroxysteroid compounds.

By hydroxysteroid dehydrogenases are generally understood those enzymes which are capable of catalyzing the reduction of keto groups to hydroxy groups or the oxidation, respectively, of hydroxy groups to the corresponding keto groups on the steroid skeleton. The oxidation or reduction, respectively, can thereby occur on the ring system of the steroid itself (e.g., 7-α hydroxysteroid dehydrogenases) or also on carbon moieties of the skeletal structure of the steroid (e.g., 20-β hydroxysteroid dehydrogenases).

Suitable hydroxysteroid dehydrogenases for the reduction of oxosteroid compounds are, for example, 3-α hydroxysteroid dehydrogenase (HSDH), 3β HSDH, 12α HSDH, 20β HSDH, 7α HSDH, 7β HSDH, 17β HSDH and 11β HSDH.

A suitable 3-α hydroxysteroid dehydrogenase is obtainable, for example, from *Pseudomonas testosteroni* (J. Biol. Chem. 276 (13), 9961-9970 (2001)) and can be used for the oxidation of 3-α-hydroxysteroids and for the reduction, respectively, of 3-ketosteroids such as, e.g., 3-keto-bile acids, progesterone, 4-androstene-3,17-dione, 5-α-androstane-3, 17-dione etc.

Suitable enzymes having 3-β hydroxysteroid dehydrogenase activity are obtainable, for example, from *Clostridium innocuum* (Applied and Environmental Microbiology, June 1989, p. 1656-1659) or from *Pseudomonas testosteroni* and can be used for the oxidation of 3-β-hydroxysteroids and for the reduction, respectively, of 3-ketosteroids such as, e.g., 3-keto-bile acids, progesterone, 4-androstene-3,17-dione, 5-α-androstane-3,17-dione etc.

A 12α HSDH is obtainable, for example, from Clostridia (Eur. J. Biochem. 196 (1991) 439-450) and can be used for the oxidation of 12α-hydroxysteroids (e.g. cholic acid) and for the reduction, respectively, of 12-ketosteroids, such as, e.g., 12-keto-bile acids (12-ketochenodeoxycholic acid, dehydrocholic acid). Enzymes from Clostridia having 12-β hydroxysteroid dehydrogenase activity are described as well (Biochim. Biophys. Acta 1988 Oct. 14; 962(3): 362-370).

Enzymes having 20-β hydroxysteroid dehydrogenase activity are obtainable, for example, from organisms of the group *Streptomyces* (The Journal of Biological Chemistry, 1977, Vol 252 No 1, January 10, 205-211) and can be used for the reduction of cortisone and cortisol derivatives (cortisone, cortisol, cortexolone, progesterone) to the corresponding 20-β-hydroxysteroids (e.g., 20-β-hydroxyprogesterone).

Corresponding enzymes having 20-α hydroxysteroid dehydrogenase activity are obtainable, for example, from Clostridia, in particular from *Clostridium scindens* (Journal of Bacteriology, June 1989, p. 2925-2932), and from *Tetrahymena pyriformis* (Biochem. J. (1994) 297, 195-200). Suitable 7-α hydroxysteroid dehydrogenases are obtainable, among other things, from organisms of the intestinal flora such as, e.g., from Clostridia (*Clostridium absonum, Clostridium sordellii*) (Journal of Bacteriology, August 1994, p. 4865-4874), from *Escherichia coli* (Journal of Bacteriology April, 1991, p. 2173-2179), from *Bacteroides fragilis* (Current Microbiology, Vol 47 (2003) 475-484), *Brucella, Eubacterium* and can be used for the oxidation of 7-α-hydroxysteroids (chenolithocholic acid) and for the reduction, respectively, of 7-ketosteroids such as, e.g., 7-keto-bile acids (ketolithocholic acid).

Corresponding enzymes having 7-β hydroxysteroid dehydrogenase activity are likewise described to be obtainable from Clostridia, from microorganisms of the family of ruminococci (J. Biochemistry 102, 1987, p. 613-619) or peptostreptococci, respectively (Biochimica and Biophysica Acta 1004, 1989, p. 230-238), from *Eubacterium aerofaciens* (Applied and Environmental Microbiology, May 1982, p. 1057-1063) and from *Xanthomonas maltophila* (Pedrini et al, Steroids 71 (2006) p. 189-198). By means of 7-β HSDH, ursodeoxycholic acid can, for example, be produced from ketolithocholic acid.

17-β hydroxysteroid dehydrogenases are known from fungi such as *Cylindrocarpon radicola* (J. Biochemistry 103, 1988, 1039-1044) and *Cochliobolus lunatus* (J. Steroid Biochem. Molec. Biol. Vol 59, 1996, No. 2, p. 205-214), from bacteria of the family of *Streptomyces* (Hoppe-Seyler's Z. Physiol. Chem, Vol. 356, 1975, 1843-1852), *Pseudomonas* (The Journal of Biological Chemistry, Vol. 252 No. 11, Jun. 10, 1977, p. 3775-3783) and *Alcaligenes* (The Journal of Biological Chemistry, Vol. 260, No. 25, Nov. 5, 1985, p. 13648-13655).

17-β hydroxysteroid dehydrogenases can, for example, be used for the oxidation of 17-β-hydroxysteroids and for the reduction, respectively, of 17-ketosteroids such as, e.g., 4-androstene-3,17-dione, androsterone, estrone.

A corresponding enzyme having 17-α hydroxysteroid dehydrogenase activity is described to be obtainable from *Eubacterium* sp. (Journal of Lipid Research, Vol. 35, 1994, p. 922-929).

11-β hydroxysteroid dehydrogenases are known from higher mammals and can be used, for example, for oxidizing cortisol to cortisone.

However, any other oxidoreductase which catalyzes oxidations and reductions, respectively, on the steroid skeleton can also be used as the hydroxysteroid dehydrogenase.

Suitable secondary alcohol dehydrogenases for regenerating the NADH or NAD, respectively, when using, e.g., 17-β hydroxysteroid dehydrogenases from *Pseudomonas testosteroni*, 3-β hydroxysteroid dehydrogenases from *Clostridium innocuum* or 7-α hydroxysteroid dehydrogenase from *Bacteroides fragilis*, are, for example, those as described above and are isolated from yeasts of the genera *Candida* and *Pichia* such as, e.g.: Carbonyl reductase from *Candida parapsilosis* (CPCR) (U.S. Pat. No. 5,523,223 and U.S. Pat. No. 5,763,236; Enzyme Microb. Technol. 1993 November; 15(11):950-8), *Pichia capsulata* (DE 10327454.4), *Pichia farinosa* (A 1261/2005, Kl. C12N), *Pichia finlandica* (EP 1179595 A1), *Candida nemodendra* (A 1261/2005, Kl. C12N), *Pichia trehalophila* (A 1261/2005, Kl. C12N), *Rhodotorula mucilaginosa* (A 1261/2005, Kl. C12N), *Lodderomyces elongisporus* (A 1261/2005, Kl. C12N) *Pichia stipidis* (A 1261/2005, Kl. C12N)

Furthermore, the regeneration of NADH can also be effected with secondary alcohol dehydrogenases/oxidoreductase as described above and isolated from bacteria of the class of actinobacteria, e.g., from *Rhodococcus erythropolis* (U.S. Pat. No. 5,523,223), *Norcardia fusca* (Biosci. Biotechnol. Biochem., 63 (10) (1999), pp. 1721-1729; Appl. Microbiol. Biotechnol. 2003 September; 62(4):380-6, Epub 2003 Apr. 26), *Rhodococcus ruber* (J. Org. Chem. 2003 Jan. 24; 8(2):402-6.) or *Microbacterium* spec. (A 1261/2005, Kl. C12N).

Suitable secondary alcohol dehydrogenases/oxidoreductases for regenerating the NADPH or NADP, respectively, when using, e.g., 12-α hydroxysteroid dehydrogenases from *Clostridium paraputrificum*, 17-α hydroxysteroid dehydrogenases from *Eubacterium* sp. or 7-α hydroxysteroid dehydrogenase from *Clostridium sordelli*, are, for example, those as described above and isolated from organisms of the order of Lactobacillales (*Lactobacillus kefir* (U.S. Pat. No. 5,200, 335), *Lactobacillus brevis* (DE 19610984 A1; Acta Crystallogr. D. Biol. Crystallogr. 2000 December; 56 Pt 12: 1696-8), *Lactobacillus minor* (DE 10119274), *Leuconostoc carnosum* (A 1261/2005, Kl. C12N) or are those as described from *Thermoanerobium brockii*, *Thermoanerobium ethanolicus* or *Clostridium beijerinckii*.

Both enzymes, hydroxysteroid dehydrogenase and oxidoreductase/alcohol dehydrogenase, are preferably used in a state of being recombinantly overexpressed in *Escherichia coli*. In the process according to the invention, both enzymes, hydroxysteroid dehydrogenase and alcohol dehydrogenase/oxidoreductase, can be used either in a completely purified state, in a partially purified state or in a state of being included in cells. The cells used can thereby be present in the native, in a permeabilized or in a lysed state.

Per kg of oxosteroid compound and hydroxysteroid compound, respectively, to be converted, 50 000 to 10 Mio U of hydroxysteroid dehydrogenase and 50 000 to 10 Mio U of alcohol dehydrogenase are used (no upper limit).

The enzyme unit 1 U thereby corresponds to the enzyme amount of hydroxysteroid dehydrogenase which is required for converting 1 μmol of oxosteroid compound per minute (min), or to the enzyme amount of alcohol dehydrogenase, respectively, which is required for oxidizing 1 μmol 2-alcohol per minute (min).

Analogically, per kg of oxosteroid compound or hydroxysteroid compound, respectively, to be converted, approx. 10 g to 500 g biological wet mass of *E. coli* containing the hydroxysteroid dehydrogenase and 10 g to 500 g biological wet mass of *E. coli* containing the alcohol dehydrogenase/oxidoreductases can be used (no upper limit).

In the described process, the regeneration of NAD(P)H is effected in an enzyme-coupled manner.

In the process according to the invention, the conversion of the oxosteroid compound or hydroxysteroid compound, respectively, preferably occurs in the two-phase system containing a 2-alcohol or a keto compound, respectively, for cofactor regeneration, a hydroxysteroid dehydrogenase, an alcohol dehydrogenase, water, cofactor and the oxosteroid compound or hydroxysteroid compound, respectively. Furthermore, additional organic solvents can also be included which are not involved in the cofactor regeneration, i.e., which do not contain any hydroxy groups oxidizable by the alcohol dehydrogenase used or any keto group, respectively, reducible by the same.

The portion of organic components not miscible with water in the two-phase system can range between 10% and 90%, preferably from 20% to 80%, based on the total volume of the reaction. The aqueous portion can range from 90% to 10%, preferably from 80% to 20%, based on the total volume of the reaction batch.

A buffer can be added to the water, for example, a potassium phosphate, tris/HCl, glycine or triethanolamine buffer having a pH value of from 5 to 10, preferably from 6 to 9. In addition, the buffer can comprise ions for the stabilization or activation of both enzymes, for instance, magnesium ions or zinc ions.

Additionally, further additives for stabilizing the enzymes hydroxysteroid dehydrogenase and alcohol dehydrogenase can also be used in the process according to the invention, such as, for example, glycerol, sorbitol, 1,4-DL-dithiothreitol (DTT) or dimethyl sulfoxide (DMSO).

The concentration of the cofactor NAD(P)H, based on the aqueous phase, ranges from 0.001 mM to 10 mM, in particular from 0.01 mM to 1.0 mM. Depending on the specific properties of the enzymes used, the temperature can range from 10° C. to 70° C., preferably from 20° C. to 35° C.

The TTN (total turn over number=mol of reduced oxosteroid compound/mol of cofactor used) achieved in the process according to the invention can thereby lie in the range of $10^2$ to $10^5$, normally, a TTN>$10^3$ is preferred.

Usually, the oxosteroid compounds to be reduced and hydroxysteroid compounds, respectively, are poorly soluble in water. During the reaction, the substrate can be present in a completely or incompletely dissolved state. If the substrate is not completely dissolved in the reaction mixture, a portion of the substrate is provided in solid form and may thus form a third solid phase. During the conversion, the reaction mixture may also temporarily form an emulsion. In the process according to the invention, the oxosteroid compound to be reduced and the hydroxysteroid compounds to be oxidized, respectively, are used in amounts of ≧50 g/l, based on the total volume of the reaction batch. Preferably, between 50 g/l and 400 g/l of oxosteroid compound/hydroxysteroid compounds, particularly preferably between 50 g/l and 200 g/l, are used.

The preferred additional organic solvents not involved in the regeneration of the cofactor are, for example, ethyl acetate, butyl acetate, tertiary butyl methyl ether, diisopropyl ether, heptane, hexane, toluene, dichloromethane or cyclohexane or mixtures thereof of different compositions.

The regeneration of NAD(P)H is achieved by oxidation of secondary alcohols of general formula $R_XR_YCHOH$ or of C4-C6-cycloalkanols, respectively. In doing so, ketones of general formula $R_XR_YC=O$ or C4-C6-cycloalkanones, respectively, are formed as reaction products. Preferred secondary alcohols are aliphatic 2-alcohols such as, e.g., isopropanol, 2-butanol, 2-pentanol, 2-hexanol, 2-heptanol, 2-octanol, 4-methyl-2-pentanol, 5-methyl-2-hexanol, but also cyclic secondary alcohols such as cyclohexanol, cyclopentanol. In principle, the use of diols such as, e.g., 1,4-cyclohexanediol, is conceivable as well.

The regeneration of NAD(P) is achieved by reduction of keto compounds of general formula $R_XR_YC=O$ or of C4-C6-cycloalkanones, respectively. In doing so, secondary alcohols of general formula $R_XR_YCHOH$ or C4-C6-cycloalkanols, respectively, are formed as reaction products. Preferred keto compounds are ketones such as, e.g., acetone, 2-butanone, 2-pentanone, 2-hexanone, 2-heptanone, 2-octanone, 4-methyl-2-pentanone, 5-methyl-2-hexanone but also cyclic ketones such as cyclohexanone, cyclopentanone. In principle, the use of diones such as, e.g., 1,4-cyclohexanedione, is conceivable as well.

The process according to the invention is carried out, for example, in a reaction vessel made of glass or metal. For this purpose, the components are transferred individually into the reaction vessel and stirred under an atmosphere of, e.g., nitrogen or air. Depending on the oxosteroid compound that is used, the reaction time ranges from 1 hour to 96 hours, in particular from 2 hours to 48 hours. In this period, the oxosteroid compound is reduced to the corresponding hydroxysteroid by at least 50%, or the hydroxysteroid is oxidized to the oxosteroid compound by at least 50%, respectively.

Below, the present invention is illustrated in further detail by way of examples.

EXAMPLES

1. Reduction of androstene-3,17-dione to 17-β-hydroxy-4-androstene-3-one (Testosterone)

A) Two-Phase System with 4-methyl-2-pentanol for Coenzyme Regeneration

For the synthesis of 17 β-hydroxy-4-androstene-3-one (testosterone), 100 mg androstene-3,17-dione dissolved in 0.4 ml 4-methyl-2-pentanol are added to 0.5 ml of a buffer (100 mM triethanolamine, pH=7, 1 mM $MgCl_2$, 10% glycerol) containing 0.1 mg NAD, 30 units of recombinant 17-β-hydroxysteroid dehydrogenase from *Pseudomonas testosteroni* (J. Steroid Biochem. Mol. Biol. 44 (2), 133-139 (1993), Pubmed P19871) and 50 units of recombinant alcohol dehydrogenase from *Pichia capsulata* (DE-A 103 27 454). The mixture is incubated at room temperature for 24 h under constant mixing. The concentration of androstene-3,17-dione in the total reaction volume amounts to approx. 100 g/l.

Upon completion of the reaction, the reaction mixture can, for example, be processed by extracting the reaction mixture with an organic solvent and subsequently removing the solvent via distillation.

After 24 h, approx. 94% of the androstene-3,17-dione used has been converted to 17-β-hydroxy-4-androstene-3-one (testosterone).

The conversion of androstene-3,17-dione to 17-β-hydroxy-4-androstene-3-one (testosterone) was monitored by gas chromatography. For this purpose, a gas chromatograph GC-17A of Shimadzu was used with a chiral separating column Lipodex E, 12m (Machery-Nagel, Düren, Germany), a flame ionization detector and helium as a carrier gas.

B) Two-phase System with butyl acetate and 2-propanol for Coenzyme Regeneration

For the synthesis of 17-p-hydroxy-4-androstene-3-one (testosterone), 100 mg androstene-3,17-dione dissolved in 0.3 ml butyl acetate and 0.1 ml 2-propanol are added to 0.5 ml of a buffer (100 mM triethanolamine, pH=7, 1 mM $MgCl_2$, 10% glycerol) containing 0.1 mg NAD, 30 units of recombinant 17-β-hydroxysteroid dehydrogenase from *Pseudomonas testosteroni* (J. Steroid Biochem. Mol. Biol. 44 (2), 133-139 (1993), Pubmed P19871) and 50 units of recombinant alcohol dehydrogenase from *Pichia capsulata* (DE-A 103 27 454). The mixture is incubated at room temperature for 24 h under constant mixing. The concentration of androstene-3,17-dione in the total reaction volume amounts to approx. 100 g/l.

Upon completion of the reaction, the reaction mixture can, for example, be processed by extracting the reaction mixture with an organic solvent and subsequently removing the solvent via distillation.

After 24 h, approx. 90-95% of the androstene-3,17-dione used has been converted to 17-β-hydroxy-4-androstene-3-one (testosterone).

2. Reduction of Ketolithocholic Acid to Chenolithocholic Acid

A) Coenzyme Regeneration with ADH from *Thermoanerobium brockii*/Two-Phase System For the synthesis of 3α-7α-dihydroxy-5-β-cholanic acid (chenodeoxycholic acid), 100 mg 3α-hydroxy-7-oxo-5-β-cholanic acid (ketolithocholic acid) in 0.5 ml methylpentanol are added to 0.2 ml of a buffer (100 mM potassium phosphate buffer, pH=8.5, 1 mM $MgCl_2$, 10% glycerol) containing 0.1 mg NADP, 10 units of recombinant 7-α-hydroxysteroid dehydrogenase from *Clostridiem scindens* (Pubmed AAB61151) and 10 units of recombinant alcohol dehydrogenase from *Thermoanerobium brockii*. The mixture is incubated at room temperature for 24 h under constant mixing. The concentration of ketolithocholic acid in the total reaction volume amounts to approx. 100 g/l.

After 24 h, approx. 90-98% of the ketolithocholic acid used has been converted to chenodeoxycholic acid.

The conversion of ketolithocholic acid to chenodeoxycholic acid was monitored by HPLC. For this purpose, a separating column EC125/4 Nucleodur 100-5 C18ec (Machery-Nagel, Düren, Germany) was used isocratically with a mixture of MeOH/water (80:20).

B) Coenzyme Regeneration with ADH from *Lactobacillus* (DE 10119274)/Two-Phase System For the synthesis of 3α-7α-dihydroxy-5-β-cholanic acid (chenodeoxycholic acid), 100 mg 3α-hydroxy-7-oxo-5-β-cholanic acid (ketolithocholic acid) in 0.5 ml octanol are added, for example, to 0.3 ml of a buffer (100 mM triethanolamine buffer, pH=7, 1 mM $MgCl_2$, 10% glycerol) containing 0.1 mg NADP, 10 units of recombinant 7-α-hydroxysteroid dehydrogenase from *Clostridium scindens* (Pubmed AAB61151) and 10 units of recombinant alcohol dehydrogenase from *Lactobacillus* (DE 10119274). The mixture is incubated at room temperature for 24 h under constant mixing. The concentration of ketolithocholic acid in the total reaction volume amounts to approx. 100 g/l.

After 24 h, approx. 70-80% of the ketolithocholic acid used has been converted to chenodeoxycholic acid.

3. Reduction of 1,4-androstadiene-3,17-dione to 17-β-hydroxy-1,4-androstadiene-3-one For the synthesis of 17-p-hydroxy-1,4-androstadiene-3-one, 100 mg 1,4-androstadiene-3,17-dione dissolved in 0.4 ml 4-methyl-2-pentanol are added to 0.5 ml of a buffer (100 mM triethanolamine, pH=7, 1 mM $MgCl_2$, 10% glycerol) containing 0.1 mg NAD, 30 units of recombinant 17-β-hydroxysteroid dehydrogenase from *Pseudomonas testosteroni* (J. Steroid Biochem. Mol. Biol. 44 (2), 133-139 (1993), Pubmed P19871) and 5 units of recombinant alcohol dehydrogenase from *Pichia capsulata* (DE-A 103 27 454). The mixture is incubated at room temperature for 24 h under constant mixing. The concentration of 1,4-androstadiene-3,17-dione in the total reaction volume amounts to approx. 100 g/l.

Upon completion of the reaction, the reaction mixture can, for example, be processed by separating the organic phase and subsequently removing the solvent via distillation.

After 24 h, approx. 90-98% of the androstene-3,17-dione used has been converted to 17-β-hydroxy-1,4-androstadiene-3-one.

The conversion of 1,4-androstadiene-3,17-dione to 17-p-hydroxy-1,4-androstadiene-3-one was monitored by gas chromatography. For this purpose, a gas chromatograph Autosystem XL of Perkin Elmer equipped with a mass spectrometer was used with an FS-capillary column Optima-5-MS (Machery-Nagel, Düren, Germany) and helium as a carrier gas.

4. Oxidation of chenolithocholic acid to ketolithocholic acid

A) Coenzyme Regeneration with ADH from *Thermoanerobium brockii*/Two-Phase System For the synthesis of 3α-hydroxy-7-oxo-5-β-cholanic acid (ketolithocholic acid), 100 mg 3α-7α-dihydroxy-5-β-cholanic-acid (chenodeoxycholic acid) in 0.5 ml methyl isobutyl ketone are added to 0.4 ml of a buffer (100 mM potassium phosphate buffer, pH=8.5, 1 mM MgCl$_2$, 10% glycerol) containing 0.1 mg NADP, 10 mg biological wet mass *E. coli* containing the overexpressed 7-α-hydroxysteroid dehydrogenase from *Clostridiem scindens* (Pubmed AAB61151) and 5 mg biological wet mass *E. coli* containing the overexpressed alcohol dehydrogenase from *Thermoanerobium brockii*. The mixture is incubated at room temperature for 24 h under constant mixing. The concentration of ketolithocholic acid in the total reaction volume amounts to approx. 100 g/l.

After 24 h, more than 80% of the chenodeoxycholic acid used has been converted to ketolithocholic acid.

The conversion of ketolithocholic acid to chenodeoxycholic acid was monitored by thin-layer chromatography.

B) Coenzyme Regeneration with ADH from *Lactobacillus* (DE 10119274)/Two-Phase System For the synthesis of 3α-hydroxy-7-oxo-5-β-cholanic acid (ketolithocholic acid), 100 mg 3α-7α-dihydroxy-5-β-cholanic-acid (chenodeoxycholic acid) in 0.7 ml methyl isobutyl ketone are added to 0.15 ml of a buffer (100 mM potassium phosphate buffer, pH=7.5, 1 mM MgCl$_2$, 10% glycerol) containing 0.1 mg NADP, 10 mg biological wet mass *E. coli* containing the overexpressed 7-α-hydroxysteroid dehydrogenase from *Clostridiem scindens* (Pubmed AAB61151) and 5 mg biological wet mass *E. coli* containing the overexpressed alcohol dehydrogenase from *Lactobacillus* (DE 10119274). The mixture is incubated at room temperature for 24 h under constant mixing. The concentration of ketolithocholic acid in the total reaction volume amounts to approx. 100 g/l.

After 24 h, more than 90% of the chenodeoxycholic acid used has been converted to ketolithocholic acid.

The invention claimed is:

1. A process for the enantioselective enzymatic reduction of an oxosteroid compound to a hydroxysteroid compound, the process comprising:
   providing an oxosteroid compound having the following steroid structure (ABCD),

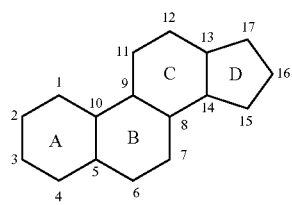

(ABCD)

wherein the ring of the steroid structure (ABCD) includes one or several heteroatoms, one or several double bonds and/or one aromatic component and has at least one oxo group at positions 3, 7, 11, 12 or 17 in the steroid structure or in the α-position at any carbon moiety attached to the steroid structure,
   reducing the oxosteroid compound with a hydroxysteroid dehydrogenase in the presence of a cofactor NADH or NADPH, characterized in that:
   (a) the oxosteroid compound is provided in the reaction at a concentration of 50 g/L,
   (b) the oxidized cofactor NAD or NADP formed by the hydroxysteroid dehydrogenase is regenerated continuously by oxidation of a secondary alcohol of formula R$_x$R$_y$CHOH, wherein R$_x$, R$_y$, independently represent a branched or unbranched C1-C8-alkyl and C$_{total}$≧3, or by oxidation of a C4-C6 cycloalkanol, and
   c) an additional oxidoreductase/alcohol dehydrogenase is used for the oxidation of the secondary alcohol of formula R$_x$R$_y$CHOH or of the cycloalkanol, respectively.

2. The process according to claim 1, characterized in that the oxosteroid compound has the structure of formula I:

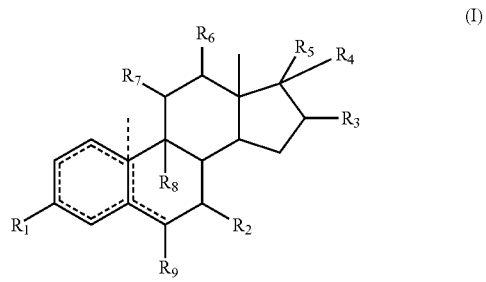

(I)

wherein
   R$_1$ represents hydrogen, a methyl group, a hydroxy group or an oxo group,
   R$_2$ represents hydrogen, a methyl group, a hydroxy group or an oxo group,
   R$_3$ represents hydrogen, a hydroxy group, an oxo group or a methyl group,
   R$_4$ represents a hydrogen or a hydroxy group,
   R$_5$ represents hydrogen, a moiety —COR$_{10}$, wherein R$_{10}$ is a C1-C4-alkyl group that is unsubstituted or substituted with a hydroxy group or a substituted group or a substituted or unsubstituted C1-C4 carboxyaklyl group,
   or R$_4$ and R$_5$ together present an oxo group,
   R$_6$ represents hydrogen, a methyl group, a hydroxy group or an oxo group,
   R$_7$ represents hydrogen, a methyl group, a hydroxyl group or an oxo group,
   R$_8$ represents hydrogen, a methyl group or a halide, and
   R$_9$ represents hydrogen, a methyl group, a hydroxy group or a halide,
   wherein at least one of R$_1$, R$_2$, R$_4$ +R$_5$, R$_6$, R$_8$ or R$_9$ is an oxo group, or R$_5$ is a moiety —COR$_{10}$, respectively,
   wherein the ring having the R$_1$ radical can be a benzene ring or a C6-ring having 0, 1, or 2 C—C double bonds.

3. The process according to claim 1, characterized in that 2-propanol, 2-butanol, 2-pentanol, 4-methyl-2-pentanol, 2-hexanol, 2-heptanol, 5-methyl-2-hexanol or 2-octanol is used as the secondary alcohol of formula R$_x$R$_y$CHOH, and cyclohexanol is used as the cycloalcohol.

4. The process according to claim 1, characterized in that the reduction is carried out in an aqueous organic two-phase system.

5. The process according to claim 4, characterized in that diethyl ether, tertiary butyl methyl ether, diisopropyl ether, dibutyl ether, ethyl acetate, butyl acetate, heptane, hexane or cyclohexane is additionally employed as an organic solvent.

6. The process according to claim 1, characterized in that the TTN (total turn over number=mol of reduced oxosteroid compound/mol of cofactor used) is ≧10$^3$.

7. The process according to claim 1, characterized in that at least 50% of the oxosteroid compound is reduced to the hydroxysteroid compound within 2 to 96 h.

8. The process according to claim 1, characterized in that the oxosteroid compound is ketolithocholic acid (formula II):

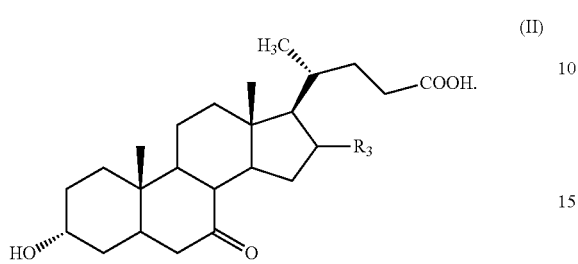

(II)

9. The process according to claim 1, characterized in that the oxosteroid compound is dexamethasone (formula III):

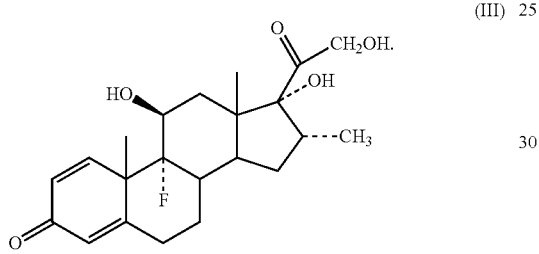

(III)

10. The process according to claim 1, characterized in that the oxosteroid compound is 4-androstene-3,17-dione (formula IV):

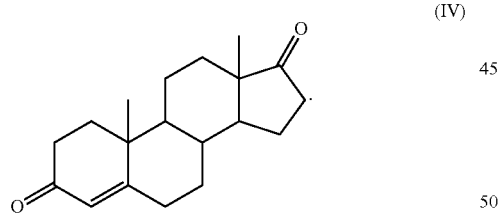

(IV)

11. The process according to claim 1, characterized in that the oxosteroid compound is 1,4-androstadiene-3,17-dione (formula V):

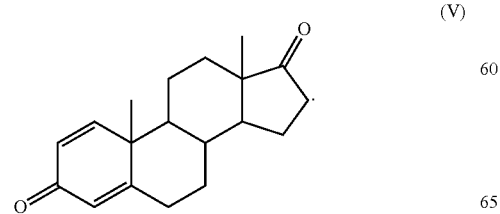

(V)

12. The process according to claim 1, characterized in that the oxosteroid compound is estrone (formula VI):

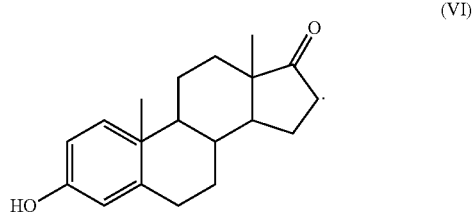

(VI)

13. The process according to claim 1, characterized in that the oxosteroid compound is pregenolone (formula VII):

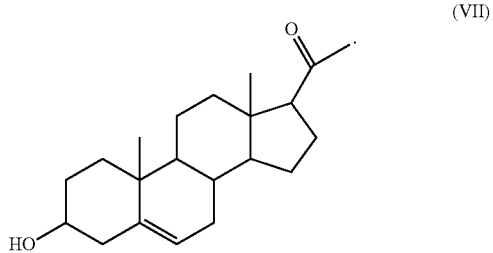

(VII)

14. The process according to claim 1, characterized in that the oxosteroid compound is cortisone (formula VIII):

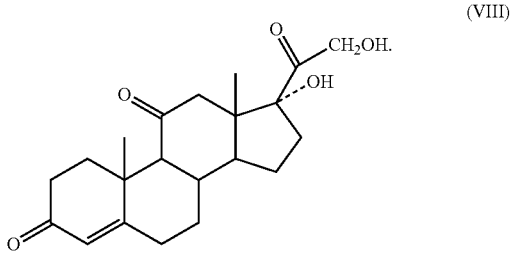

(VIII)

15. A process for the enzymatic oxidation of a hydroxysteroid compound to an oxosteroid compound, the process comprising:
providing a hydroxysteroid compound having the following steroid structure (ABCD),

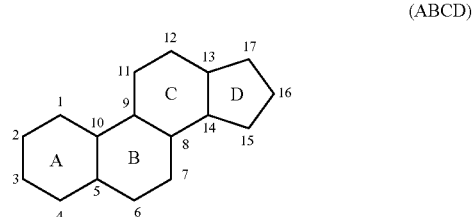

(ABCD)

wherein the ring of the steroid structure (ABCD) includes one or several heteroatoms, one or several double bonds and/or one aromatic component and has at least one hydroxy group at positions 3, 7, 11, 12 or 17 in the steroid structure or in the α-position at any carbon moiety attached to the steroid structure, oxidizing the hydroxysteroid compound with a hydroxysteroid dehydrogenase in the presence of a cofactor NAD or NADP, characterized in that:
(a) the hydroxysteroid compound is provided in the reaction at a concentration of $\geq 50$ g/L,
(b) the reduced cofactor NADH or NADPH formed by the hydroxysteroid dehydrogenase is regenerated continuously by reduction of a keto compound of formula $R_X R_Y CO$, wherein $R_X$, $R_Y$, independently represent a branched or unbranched C1-C8-alkyl and $C_{total} \geq 3$, or by reduction of a C4-C6 cycloalkanone, and
(c) an additional oxidoreductase/alcohol dehydrogenase is used for the reduction of the keto compound of formula $R_x R_y CO$ or of the cycloalkanone, respectively.

16. The process according to claim 15, characterized in that the hydroxysteroid has the structure of formula I:

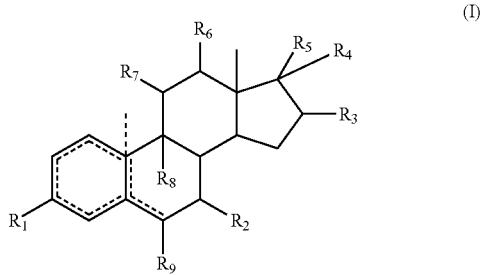

(I)

wherein
$R_1$ represents hydrogen, a methyl group, a hydroxyl group or an oxo group,
$R_2$ represents hydrogen, a methyl group, a oxo group or a hydroxy group,
$R_3$ represents hydrogen, a hydroxyl group, an oxo group or a methyl group,
$R_4$ represents a hydrogen or a hydroxy group,
$R_5$ represents hydrogen, a moiety —$COR_{10}$, wherein $R_{10}$ is a C1-C4-alkyl group that is unsubstituted or substituted with a hydroxy group or a substituted group or a substituted or unsubstituted C1-C4 carboxyaklyl group, or $R_4$ and $R_5$ together present an oxo group,
$R_6$ represents hydrogen, a methyl group, an oxo group or a hydroxy group,
$R_7$ represents hydrogen, a methyl group, an oxo group or a hydroxy group,
$R_8$ represents hydrogen, a methyl group or a halide, and
$R_9$ represents hydrogen, a methyl group, a hydroxy group, an oxo group or a halide,
wherein at least one of $R_1$, $R_2$, $R_4$, $R_6$, $R_7$, $R_8$ or $R_9$ is a hydroxy group,
wherein the ring having the $R_1$ radical can be a benzene ring or a C6-ring having 0, 1, or 2 C—C double bonds.

17. The process according to claim 15, characterized in that acetone, 2-butanone, 2-pentanone, 4-methyl-2-pentanone, 2-hexanone, 2-heptanone, 5-methyl-2-hexanone or 2-octanone is used as the ketone of formula $R_x R y CO$, and cyclohexanone is used as the cycloalkanone.

18. The process according to claim 15, characterized in that the oxidation is carried out in an aqueous organic two-phase system.

19. The process according to claim 18, characterized in that diethyl ether, tertiary butyl methyl ether, diisopropyl ether, dibutyl ether, ethyl acetate, butyl acetate, heptane, hexane or cyclohexane is additionally employed as an organic solvent.

20. The process according to claim 15, characterized in that the TTN (total turn over number=mol of oxidized hydroxysteroid compound/mol of cofactor used) is $\geq 10^3$.

21. The process according to claim 15, characterized in that at least 50% of the hydroxysteroid compound is oxidized to the oxosteroid compound within 2 to 96 h.

* * * * *